(12) United States Patent
Hwang et al.

(10) Patent No.: US 12,023,329 B2
(45) Date of Patent: Jul. 2, 2024

(54) METHODS FOR THE TREATMENT OF DISEASES ASSOCIATED WITH ACTIVATION OF INFLAMMASOMES

(71) Applicant: Chang Gung University, Taoyuan (TW)

(72) Inventors: Tsong-Long Hwang, New Taipei (TW); Ya-Xuan Wang, Tainan (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 981 days.

(21) Appl. No.: 17/002,784

(22) Filed: Aug. 26, 2020

(65) Prior Publication Data

US 2022/0062270 A1    Mar. 3, 2022

(51) Int. Cl.
*A61K 31/4709*      (2006.01)
*A61P 1/16*      (2006.01)
*A61P 11/00*      (2006.01)

(52) U.S. Cl.
CPC ............ *A61K 31/4709* (2013.01); *A61P 1/16* (2018.01); *A61P 11/00* (2018.01)

(58) Field of Classification Search
CPC ......... A61K 31/4709; A61P 1/16; A61P 11/00
See application file for complete search history.

(56) References Cited

U.S. PATENT DOCUMENTS

2020/0215066 A1    7/2020    Pendergast et al.

FOREIGN PATENT DOCUMENTS

CN      106822128 A      6/2017

OTHER PUBLICATIONS

Cortes et al., 102(3) Haematologica 519-528 (2017) (Year: 2017).*
Laudisi et al., 11 Cell. & Mol. Immunology 129-131 (2014) (Year: 2014).*

* cited by examiner

*Primary Examiner* — Timothy R Rozof
(74) *Attorney, Agent, or Firm* — Cheng-Ju Chiang

(57) ABSTRACT

Disclosed herein is a method of treating diseases and/or disorders associated with the activation of inflammasomes. The method includes administering to a subject in need thereof an effective amount of 4-[4-[(5-tert-butyl-2-quinolin-6-ylpyrazol-3-yl)-carbamoylamino]-3-fluorophenoxy]-N-methylpyridine-2-carboxamide, a salt, a solvate or an ester thereof.

4 Claims, 11 Drawing Sheets

METHODS FOR THE TREATMENT OF DISEASES ASSOCIATED WITH ACTIVATION OF INFLAMMASOMES

BACKGROUND OF THE INVENTION

1. Field of the Invention

The present disclosure in general relates to novel uses of a tyrosine kinase inhibitor, particularly, the use of 4-[4-[(5-tert-butyl-2-quinolin-6-ylpyrazol-3-yl)-carbamoylamino]-3-fluorophenoxy]-N-methylpyridine-2-carboxamide in treating diseases and/or disorders associated with activation of inflammasomes.

2. Description of Related Art

Inflammasomes are innate immune system receptors that induce inflammation in response to infection and molecules derived from host proteins, thus have been linked to a variety of autoinflammatory and autoimmune diseases, including neurodegenerative diseases (e.g., multiple sclerosis, Alzheiher's disease, Parkinson's disease and etc.) and metabolic disorders (e.g., atherosclerosis, type II diabetes, obesity and etc.). Accordingly, an agent exhibiting inhibitory effect towards activation of inflammasomes would be useful for treating diseases and/or disorders associated with activation of inflammasomes.

SUMMARY OF THE INVENTION

The present disclosure provides novel use of a tyrosine kinase inhibitor, 4[-4-[(5-tert-butyl-2-quinolin-6-ylpyrazol-3-yl)-carbamoylamino]-3-fluorophenoxy]-N-methylpyridine-2-carboxamide (or rebastinib), which is found to be a powerful agent that suppresses the activation of inflammasomes, thus rebastinib may serve as a candidate drug for the development of a medicament for treating diseases and/or disorders associated with the activation of inflammasomes.

Accordingly, the first aspect of the present disclosure is directed to a method of treating a subject having a disease associated with activation of inflammasomes. The method includes administering to the subject an effective amount of 4-[4-[(5-tert-butyl-2-quinolin-6-ylpyrazol-3-yl)-carbamoylamino]-3-fluorophenoxy]-N-methylpyridine-2-carboxamide, a salt, a solvate or an ester thereof.

According to embodiments of the present disclosure, the disease associated with activation of inflammasomes may be an autoinflammatory disease, a cancer, an infectious disease, an inflammatory disease, a metabolic disorder, a neurodegenerative disease, or a tissue injury.

Exemplary autoinflammatory disease that may be treated by the present method includes, but is not limited to, Addison's disease, autoimmune thyroid disorders, coeliac disease, multiple sclerosis, psoriasis, rheumatoid arthritis, Type I diabetes, systemic lupus erythematosus (SLE), systemic sclerosis, and vitiligo.

Exemplary cancer that may be treated by the present method includes, but is not limited to, B-cell lymphoma, breast cancer, cervical cancer, colorectal cancer, endometrial cancer, gastric cancer, glioblastoma, Hodgkin's lymphoma, prostate cancer, and skin cancer.

Exemplary infectious disease that may be treated by the present method includes, but is not limited to, bacterial, fungal or viral infections, sepsis, and septic shock. In some embodiments, the viral infection is hepatitis B.

Exemplary inflammatory disease that may be treated by the present method includes, but is not limited to, atopic dermatitis (AD), asthma, Blau syndrome, Crohn's disease, Cryopyrin-associated periodic syndrome (CAPS), chronic obstructive pulmonary disease (COPD), gaut, giant cell arteries, hepatitis, inflammatory bowel disease, and pulmonary fibrosis.

Exemplary metabolic disorder that may be treated by the present method includes, but is not limited to, atherosclerosis, arthritis, obesity, and type II diabetes.

Exemplary neurodegenerative disease that may be treated by the present method includes, but is not limited to, Alzheimer's disease, Parkinson disease, and the like.

Exemplary tissue injury that may be treated by the present method includes, but is not limited to, acute liver failure, acute lung injury (ALI), adult respiratory distress syndrome (ARDS), etc. Exemplary ALI/ARDS that may be treated by the present method includes, but is not limited to, transfusion-related lung injury, ventilator-induced lung injury, bacteria-induced lung injury, virus-induced lung injury, etc. In some preferred embodiments, the tissue injury is acute liver failure. In other preferred embodiments, the tissue injury is ALI/ARDS.

According to embodiments of the present disclosure, the 4-[4-[(5-tert-butyl-2-quinolin-6-ylpyrazol-3-yl)-carbamoylamino]-3-fluorophenoxy]-N-methylpyridine-2-carboxamide is administered to the subject in the amount of 0.01 to 100 mg/Kg. Preferably, the 4-[4-[(5-tert-butyl-2-quinolin-6-ylpyrazol-3-yl)-carbamoylamino]-3-fluorophenoxy]-N-methylpyridine-2-carboxamide is administered to the subject in the amount of 0.1 to 80 mg/Kg.

According to embodiments of the present disclosure, the subject suitable to be treated by the present method is a mammal; preferably, a human.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

BRIEF DESCRIPTION OF THE DRAWINGS

The accompanying drawings, which are incorporated in and constitute a part of the specification, illustrate various example systems, methods and other exemplified embodiments of various aspects of the invention. The present description will be better understood from the following detailed description read in light of the accompanying drawings, where, FIG. 1 Rebastinib inhibited nigericin-induced interleukin-1β (IL-1β) secretion in LPS-primed d-THP-1 cells. LPS-primed d-THP-1 cells were incubated with DMSO (0.1%, as control), rebastinib (0.01-1 μM), or glibenclamide (50 μM) for 30 min, and then stimulated with or without nigericin (5 μM) for 30 min. The concentration of IL-1β in cell supernatant was analyzed using ELISA kits. Data are expressed as mean±S.E.M. (n=6). ** p<0.01 compared with control.

DETAILED DESCRIPTION OF THE PREFERRED EMBODIMENTS

Figure 1:
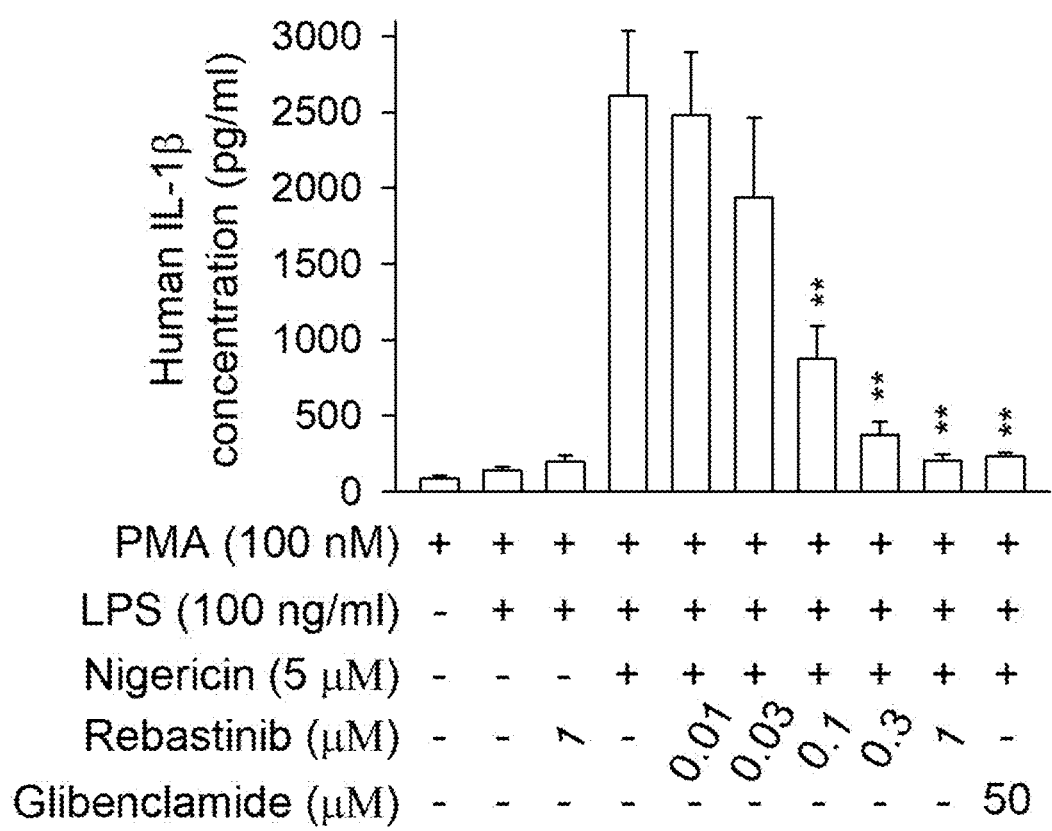

The detailed description provided below in connection with the appended drawings is intended as a description of the present disclosure and is not intended to represent the only forms in which the present disclosure may be constructed or utilized.

1. Definitions

The term "salt" refers to pharmaceutical acceptable salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemi sulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "administered", "administering" or "administration" are used interchangeably herein to refer a mode of delivery, including, without limitation, intravenously, intramuscularly, intraperitoneally, intraarterially, intracranially, or subcutaneously administering an agent (e.g., a compound or a composition) of the present invention. In some embodiments, the compound of the present disclosure or a salt, a solvate thereof is formulated into tablets for oral administration. In other embodiments, t the compound of the present disclosure or a salt, a solvate thereof is formulated into powders for mixed with suitable carrier (e.g., buffer solution) before use, such as intravenous injection.

An "effective amount" of a compound described herein (either taken alone or in combination of another agent) refers to an amount sufficient to elicit the desired biological response, e.g., inhibiting the activation of inflammasomes, or alleviating a target disease described herein or a symptom associated with the disease. As will be appreciated by those of ordinary skill in this art, the effective amount of a compound described herein may vary depending on such factors as the desired biological endpoint, the pharmacokinetics of the compound, the condition being treated, the mode of administration, and the age and health of a subject. In some examples, an effective amount can be a therapeutically effective amount, which refers to an amount of a therapeutic agent, alone or in combination with other therapies, sufficient to provide a therapeutic benefit in the treatment of a condition or to delay the onset or minimize one or more symptoms associated with the condition. The term "therapeutically effective amount" can encompass an amount that improves overall therapy, reduces or avoids symptoms, signs, or causes of the condition, and/or enhances the therapeutic efficacy of another therapeutic agent. In other examples, the effective amount can be a prophylactically effective amount. A prophylactically effective amount of a compound means an amount of a therapeutic agent, alone or in combination with other agents, which provides a prophylactic benefit in the prevention of the condition. For example, a "prophylactically effective amount" of a compound can be an amount sufficient to prevent or delay the onset of a condition, or one or more symptoms associated with the condition or prevent its recurrence. It may also be an amount that improves overall prophylaxis or enhances the prophylactic efficacy of another prophylactic agent.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Use of the Compound of the Present Invention

The present disclosure lies in the unexpected discovery of a tyrosine kinase inhibitor, 4-[4-[(5-tert-butyl-2-quinolin-6-ylpyrazol-3-yl)-carbamoylamino]-3-fluorophenoxy]-N-methylpyridine-2-carboxamide (or rebastinib), which possesses inhibitory effect toward stimulant of inflammasomes. Accordingly, rebastinib may be used as a candidate compound for the development of medicaments suitable for treating diseases and/or conditions associated with the activation of inflammasomes, such as autoinflammatory diseases, autoimmune diseases, and the like.

Accordingly, it is the first aspect of the present disclosure to provide a method of treating a subject suffering from diseases and/or conditions associated with the activation of inflammasomes. The method comprises administering to the subject an effective amount of 4-[4-[(5-tert-butyl-2-quinolin-6-ylpyrazol-3-yl)-carbamoylamino]-3-fluorophenoxy]-N-methylpyridine-2-carboxamide, a salt, a solvate or an ester thereof.

The compound of the present invention is available commercially or may be produced by any methods known in the related art. Bioactivity analysis of the present compound indicates that it is a powerful inhibitory agent of inflammasomes stimulant, thereby suppresses pyroptosis and/or formation of ASC speck. Furthermore, the present compound possesses no cytotoxicity, and significantly reduces the level of aspartate transaminase (AST), alanine transaminase (ALT), and creatinine (CRE) in subjects suffering from liver injury. Findings of the present disclosure confirm that the present compound may serve as a candidate for the development of medicaments suitable for treating diseases and/or disorders associated with activation of inflammasomes.

According to embodiments of the present disclosure, the disease associated with activation of inflammasomes may be an autoinflammatory disease, a cancer, an infectious disease, an inflammatory disease, a metabolic disorder, a neurodegenerative disease, or tissue injury.

Exemplary autoinflammatory disease that may be treated by the present method includes, but is not limited to, Addison's disease, autoimmune thyroid disorders, coeliac disease, multiple sclerosis, psoriasis, rheumatoid arthritis, Type I diabetes, SLE, systemic sclerosis, and vitiligo.

Exemplary cancer that may be treated by the present method includes, but is not limited to, B-cell lymphoma, breast cancer, cervical cancer, colorectal cancer, endometrial cancer, gastric cancer, glioblastoma, Hodgkin's lymphoma, prostate cancer, and skin cancer.

Exemplary infectious disease that may be treated by the present method includes, but is not limited to, bacterial, fungal or viral infections, sepsis, and septic shock. In some embodiments, the viral infection is hepatitis B.

Exemplary inflammatory disease that may be treated by the present method includes, but is not limited to, AD, asthma, Blau syndrome, Crohn's disease, CAPS, COPD, ALI, ARDS, gaut, giant cell arteries, hepatitis, inflammatory bowel disease, and pulmonary fibrosis.

Exemplary metabolic disorder that may be treated by the present method includes, but is not limited to, atherosclerosis, arthritis, obesity, and type II diabetes.

Exemplary neurodegenerative disease that may be treated by the present method includes, but is not limited to, Alzheimer's disease, Parkinson disease, and the like.

Exemplary tissue injury that may be treated by the present method includes, but is not limited to, acute liver failure, and ALI/ARDS. In some preferred embodiments, the tissue injury is acute liver failure. In other preferred embodiments, the tissue injury is ALI/ARDS, which may be transfusion-related lung injury, ventilator-induced lung injury, bacteria-induced lung injury, virus-induced lung injury, and etc.

According to embodiments of the present disclosure, the compound of the present disclosure, that is, 4-[4-[(5-tert-butyl-2-quinolin-6-ylpyrazol-3-yl)-carbamoylamino]-3-fluorophenoxy]-N-methylpyridine-2-carboxamide, is administered to the subject in the amount of 0.01 to 100 mg/Kg, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 mg/Kg; preferably, the 4-[4-[(5-tert-butyl-2-quinolin-6-ylpyrazol-3-yl)-carbamoylamino]-3-fluorophenoxy]-N-methylpyridine-2-carboxamide is administered to the subject in the amount of 0.1 to 80 mg/Kg, such as 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 mg/Kg. In one preferred embodiment, the 4-[4-[(5-tert-butyl-2-quinolin-6-ylpyrazol-3-yl)-carbamoylamino]-3-fluorophenoxy]-N-methylpyridine-2-carboxamide is administered to the subject in the amount of 0.8 mg/Kg. In another preferred embodiment, the 4-[4-[(5-tert-butyl-2-quinolin-6-ylpyrazol-3-yl)-carbamoylamino]-3-fluorophenoxy]-N-methylpyridine-2-carboxamide is administered to the subject in the amount of 0.5 mg/Kg. The effective amount of a compound may be administered in one or more doses for one or several days (depending on the mode of administration).

The present compound may also be formulated with suitable carriers or excipients for a suitable administration route, e.g., orally, parenterally, by inhalation spray, topically, rectally, nasally, buccally, vaginally or via an implanted reservoir. The term "parenteral" as includes subcutaneous, intracutaneous, intravenous, intramuscular, intraarticular, intraarterial, intrasynovial, intrasternal, intrathecal, intralesional and intracranial injection or infusion techniques.

A sterile injectable formulation, e.g., a sterile injectable aqueous or oleaginous suspension, can be formulated according to techniques known in the art using suitable dispersing or wetting agents (such as Tween® 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A formulation suitable for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the compound of the present disclosure can be suspended or dissolved in an oily phase combined with emulsifying or suspending agents. If desired, certain sweetening, flavoring, or coloring agents can be added. A nasal aerosol or inhalation formulation can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. The compound of the present disclosure can also be administered in the form of suppositories for rectal administration.

Pharmaceutically acceptable carriers or excipients that may be included in a formulation comprising the compound of the present disclosure include inert diluents, solubilizing agents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the pharmaceutical composition.

An excipient present in an inventive formulation must be "pharmaceutically acceptable" in the sense that the excipient is compatible with the active ingredient of the pharmaceutical composition (and preferably, capable of stabilizing the pharmaceutical composition) and not deleterious to a subject to whom the pharmaceutical composition is administered. For example, solubilizing agents such as cyclodextrins, which may form specific, more soluble complexes with the compounds of the invention, can be utilized as pharmaceutically acceptable excipients for delivery of the compounds of the invention into the subject. Examples of other pharmaceutically acceptable excipients include colloidal silicon dioxide, magnesium stearate, cellulose, sodium lauryl sulfate, and D&C Yellow #10.

Also disclosed herein are kits (e.g., pharmaceutical packs) comprising the compound described herein, and a container (e.g., a vial, ampule, bottle, syringe, and/or dispenser package, or other suitable container). In some embodiments, the kits may include a second container comprising a pharmaceutically acceptable excipient for dilution or suspension of an inventive formulation. In some embodiments, the inventive formulation or compound provided in the first container and the second container are combined to form one unit dosage form.

In certain embodiments, a kit as described herein is for use in inhibiting the activation of inflammasomes in cells. In certain embodiments, a kit as described herein is for use in treating any of the target diseases as described herein (e.g., an inflammatory disease) in a subject in need thereof. Any of the kits described herein can thus include instructions for administering the compound or pharmaceutical composition contained therein. A kit of the invention may also include information as required by a regulatory agency such as the FDA. In certain embodiments, the kit and instructions provide for treating a disease described herein. In certain embodiments, the kit and instructions provide for preventing a disease described herein. A kit of the invention may include one or more additional pharmaceutical agents described herein as a separate composition.

A "subject" to be treated by the method described herein can be a human subject (e.g., a pediatric subject such as an infant, a child, or an adolescent, or an adult subject such as a young adult, middle-aged adult, or senior adult), or a non-human animal, such as dogs, cats, cows, pigs, horses, sheep, goats, rodents (e.g., mice, rats), and non-human primates (e.g., cynomolgus monkeys, rhesus monkeys). The non-human mammal may be a transgenic animal or genetically engineered animal. In some examples, the subject is a human patient having a target disease as described herein (i.e., autoinflammatory disease, a cancer, an infectious disease, an inflammatory disease, a metabolic disorder, a neurodegenerative disease, or a condition secondary to the listed diseases), suspected of having the disease, or is at risk for the disease. In some embodiments, the subject is a human or non-human mammal having, suspected of having a condition secondary to activation of inflammasomes (e.g., acute liver failure).

Also described herein are methods for inhibiting the activation of inflammasomes in cells. Such method may comprise contacting the compound as described herein with cells in an amount effective to inhibit the activation of inflammasomes. The amount of the compound can be sufficient to inhibit at least 20% (e.g., 30%, 40%, 50%, 60%, 70%, 80%, 90%, or 95%) of the activity of a stimulant of inflammasomes formation. In some embodiments, the methods can be performed in vitro. In other embodiments, they can be performed in vivo by administering the compound to a subject in need of the treatment as described herein.

It will be also appreciated that a compound or formulation, as described herein, can be used in combination with one or more additional agents (e.g., therapeutically and/or prophylactically active agents) in any of the methods described herein. The compound or formulation can be administered in combination with additional agents that improve their activity (e.g., activity (e.g., potency and/or efficacy) in treating a disease described herein in a subject in need thereof, in preventing a disease described herein in a subject in need thereof, in inhibiting the activity of a stimulant of inflammasomes activation in a subject. It will also be appreciated that the therapy employed may achieve a desired effect for the same disorder, and/or it may achieve different effects.

The present invention will now be described more specifically with reference to the following embodiments, which are provided for the purpose of demonstration rather than limitation. While they are typically of those that might be used, other procedures, methodologies, or techniques known to those skilled in the art may alternatively be used.

EXAMPLES

Materials and Methods
Cell Culture.

Human monocytic cell line THP-1 was purchased from American Type Culture Collection (ATCC) and maintained in RPMI-1640 Medium supplemented with 10% fetal bovine serum (FBS), 1% antibiotic-antimycotic solution, 0.1% (β-mercaptoethanol ((β-ME), and phenol red indicator in an incubator at 37° C. with 5% $CO_2$. The medium was changed every 2-3 days.

Induction of Macrophage-Like Cells from THP-1 Cells

To induce differentiation, THP-1 cells (cell density was about $5 \times 10^5$/mL) was cultivated in a serum-free medium containing 100 nM of phorbol 12-myristate 13-acetate (PMA) for about 4 hr. Then, the PMA-containing medium was replaced with a fresh RPMI-1640 medium, and the cultivation was continued for another 2 days to allow the THP-1 cells to differentiate into macrophage-like cells, hereafter termed "d-THP-1 cells."

Induction of Inflammasomes and Release of IL-1β and IL-18 d-THP1 cells were first treated with 100 ng/mL of lipopolysaccharide (LPS) for 3 hr, then LPS-containing medium was replaced by a fresh medium. After incubation for 30 min, various concentrations of the tested compounds were added for another 30 min and then various stimuli (i.e., nigericin, monosodium urate (MSU), and imiquimod (IMQ)) were independently added to the medium to induce the formation of inflammasomes, and the release of IL-1β and IL-18.

Determination of the Level of IL-1β and IL-18

The level of IL-1β and IL-18 was independently determined by ELISA assay kit (R&D system) in accordance with the manufacturer's protocol. The level of IL-10 and IL-18 was determined from the 450 and 540 nm absorbance measured by Multiskan GO multiplate reader.

Cytotoxicity Assay

Cytotoxicity was determined by the measurement of lactate dehydrogenase (LDH), which is a cytosolic enzyme that is released only when the cell is dead. Briefly, supernatant from d-THP-1 cells treated with or without the tested compound or Triton-X-100 (0.1%. as total LDH) was collected. LDH substrate was added to a test tube containing the supernatant, the mixture was incubated in the dark for 30 min, then absorbance at 490 nm was measured. Cytotoxicity was determined by percentage of LDH released/total LDH in the cell.

Fluorescent Images d-THP-1 cells (treated with LPS, the tested compound, and the stimulant as described above or untreated) were fixed by 4% paraformaldehyde, washed with PBS (3 times), treated with Triton-X-100 (0.1%) for 10 min, washed with PBS (3 times), added 5% BSA for 1 hr, then washed with PBS (3 times) before the primary antibody (anti-ASC) was added. The primary anti-ASC antibody labeled cells were incubated at 4° C. overnight, then was labeled with the secondary antibody at RT for 1 hr, washed with PBS (3 times), added Hoechst 33342, washed with PBS (3 times), added ProLong™ Gold antifade reagent, then photographed using Fluorescent Microscope (IX81 Olympus, with Lumen 200 Fluorescence Illumination System).

Observing Pyroptosis by Use of Field Emission Scanning Electron Microscopy d-THP-1 cells (treated with LPS, the tested compounds, and the stimulant as described above or untreated) were fixed, in sequence, by use of 4% paraformaldehyde and 2.5% glutaraldehyde, respectively for 10 min, washed with PBS, then reacted with osmium tetroxide ($OsO_4$) for 30 min; the cells were thoroughly washed with distilled water, then incubated with tannic acid for 30 min. Dehydrating the cells by a gradient of ethanol solution, in which the concentration of ethanol was gradually increased from 30% to 50%, 70%, 80%, 90% and 100%. Repeated the 100% ethanol dehydration step 3 times. The specimens were then dried with a mixture of $CO_2$ and ethanol supercritical condition using Critical Point Dryer (CPD) (LEICAME CPD 300). The dried specimens were subsequently fixed on an alumina platform, and sputted with gold ions (ion sputter, JEOL JFC-1100E, operated at 1-2 mA for 60 sec) before subjecting to observation under Field Emission Scanning Electron Microscope (FE-SEM).

Animals.

C57BL/6 mice (7-10-week-old, each weighted about 20-25 g) were maintained in micro-isolator units on a standard laboratory diet. Animals were housed under humidity- and temperature-controlled conditions and the light/dark cycle was set at 12-hr intervals, maintained under specified and opportunistic pathogen-free conditions. All animal studies were conducted under protocol approved by the Animal Care and Use Committee of Chang Gung University (Taipei, Taiwan).

Animal Model of Acute Liver Failure

Mice were randomly divided into 4 groups. The test compound rebastinib (5 or 10 mg/Kg) or a control solvent (80% saline, 10% ethanol, 10% Tween-20) was injected through the tail vein of each mice. The mice were allowed to rest for 1 hr, then LPS (40 μg/mL)/D-GalN (400 mg/Kg) was injected through abdominal space for 5 hr to induce acute liver failure. Blood samples and tissue samples were respectively collected. Blood samples were analyzed for their respective levels of LDH, AST, ALT, BUN, and CRE. The livers were fixed in 10% formalin for tissue section. The liver sections were stained with hematoxylin and eosin (H&E).

Animal Model of ALI

ALI was induced by intra-tracheal spray of 2 mg/kg LPS in 7-8 weeks old C57BL/6 mice. Mice were fasted overnight and then intravenously injected with 50 ul of rebastinib (10 mg/kg) or an equal volume of solvent (vehicle). After 1 hr, mice were instilled with an intra-tracheal spray of 2 mg/kg LPS (dissolved in 40 μl 0.9% saline) or 0.9% saline under anesthesia. 5 hr later, mice were sacrificed and the lungs were collected. The lungs were fixed in 10% formalin for tissue section. The lung sections were stained with hematoxylin and eosin (H&E).

Figure 2:
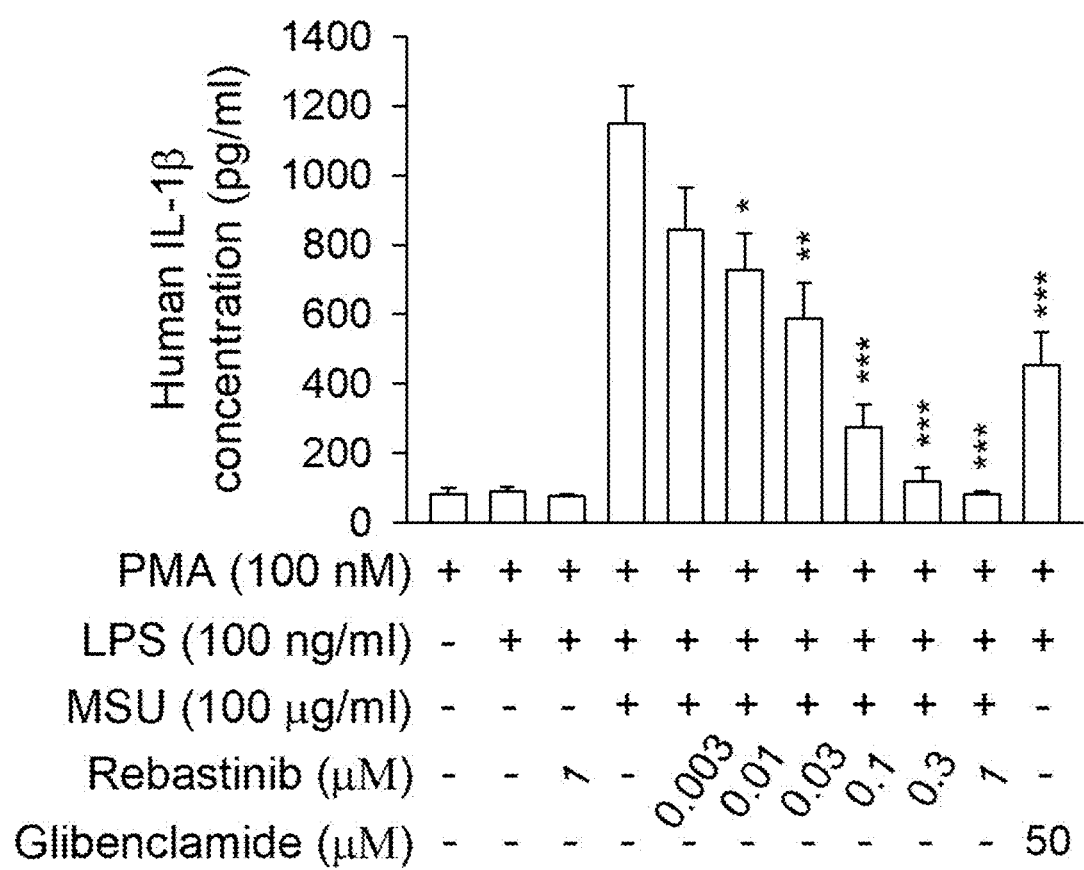
FIG. 2 Rebastinib inhibited monosodium urate (MSU)-induced IL-1β secretion in LPS-primed d-THP-1 cells. LPS-primed d-THP-1 cells were incubated with DMSO (0.1%, as control), rebastinib (0.003-1 μM), or glibenclamide (50 μM) for 30 min, and then stimulated with or without MSU (100 μg/ml) for 4 hr. The concentration of IL-1β in cell supernatant was analyzed using ELISA kits. Data are expressed as mean±S.E.M. (n=6). * p<0.05;  p<0.01; * p<0.001 compared with control.
Figure 3:
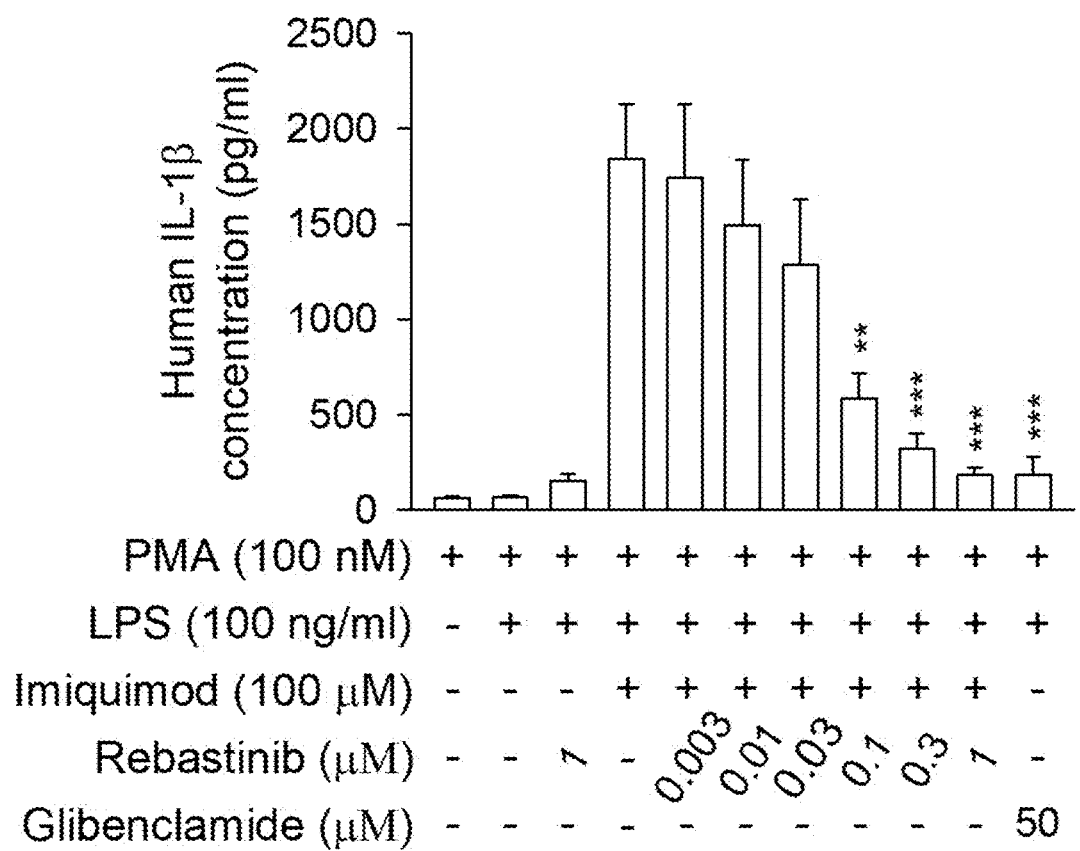
FIG. 3 Rebastinib inhibited imiquimod-induced IL-1β secretion in LPS-primed d-THP-1 cells. LPS-primed d-THP-1 cells were incubated with DMSO (0.1%, as control), rebastinib (0.003-1 µM), or glibenclamide (50 µM) for 30 min, and then stimulated with or without imiquimod (IMQ, 100 µM) for 2 hr. The concentration of IL-1β in cell supernatant was analyzed using ELISA kits. Data are expressed as mean±S.E.M. (n=6).  p<0.01; * p<0.001 compared with control.

Example 1 the Present Compound Inhibited Nigericin-Induced IL-1β Secretion in LPS-Primed d-THP-1 Cells In this example, the effect of the present compound (i.e., rebastinib) on the release of IL-1β from LPS primed macrophage-like cells (i.e., d-THP-1 cells) was investigated. To this purpose, d-THP-1 cells were first primed with LPS (100 ng/mL), then treated with the present compound at various concentrations (i.e., 0.003, 0.01, 0.03, 0.1, 0.3 or 1 μM) or glibenclamide (50 μM, positive control), and finally stimulated with a stimulant (i.e., nigericin (5 μM), MSU (100 μg/mL) or IMQ (100 μM). Results are illustrated in FIGS. 1 to 3.

As depicted, nigericin resulted in significant release of IL-1β from LPS-primed d-THP-1 cells, and the release was significantly reduced by the treatment of the present compound (FIG. 1). Similarly, MSU and IMQ also resulted in massive release of IL-1β, which were independently suppressed by the present compound (FIGS. 2 and 3).

Example 2 the Present Compound Inhibited Nigericin-Induced IL-18 Secretion in LPS-Primed d-THP-1 Cells In this example, the effect of the present compound (i.e., rebastinib) on the release of IL-18 from LPS primed macrophage-like cells (i.e., d-THP-1 cells) was investigated. To this purpose, d-THP-1 cells were first primed with LPS (100 ng/mL), then treated with the present compound at various concentrations (i.e., 0.01, 0.03, 0.1, 0.3 or 1 μM) or glibenclamide (50 μM, positive control), and finally stimulated with nigericin (5 μM). Results are illustrated in FIG. 4.

Figure 4:
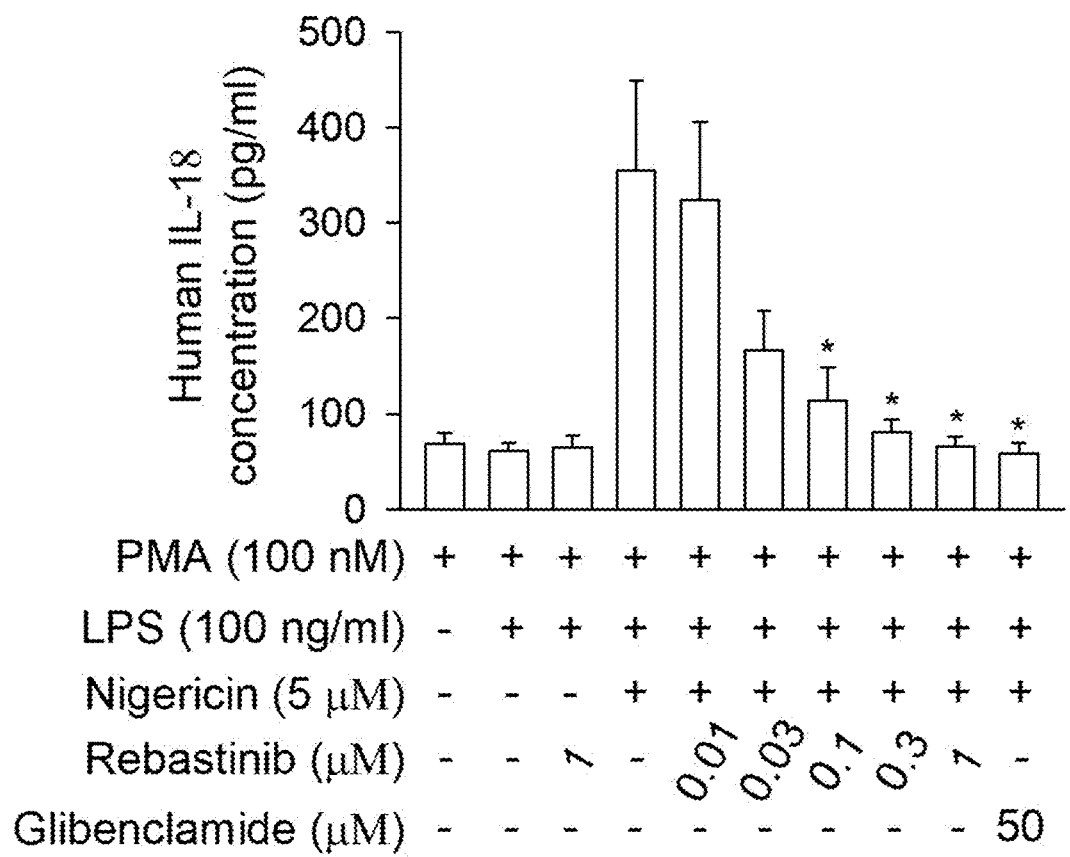
FIG. 4 Rebastinib inhibited nigericin-induced interleukin-18 (IL-18) secretion in LPS-primed d-THP-1 cells. LPS-primed d-THP-1 cells were incubated with DMSO (0.1%, as control), rebastinib (0.01-1 µM), or glibenclamide (50 µM) for 30 min, and then stimulated with or without nigericin (5 µM) for 30 min. The concentration of IL-18 in cell supernatant was analyzed using ELISA kits. Data are expressed as mean±S.E.M. (n=6). * p<0.05 compared with control.

As depicted, nigericin resulted in significant release of IL-18 from LPS-primed d-THP-1 cells, and the release was significantly reduced by the treatment of the present compound (FIG. 4).

Example 3 Cytotoxicity Study of the Present Compound

Figure 5:
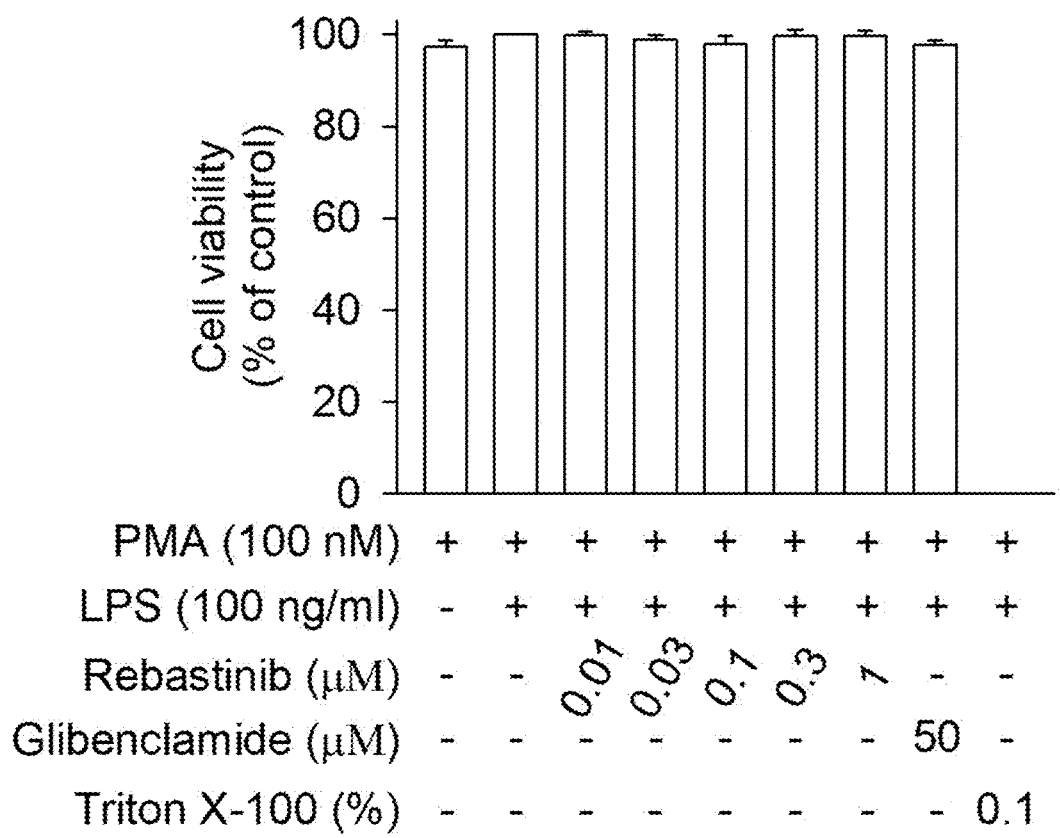
FIG. 5 Rebastinib did not alter cell viability in LPS-primed d-THP-1 cells. LPS-primed d-THP-1 cells were incubated with DMSO (0.1%, as control), rebastinib (0.01-1 µM), glibenclamide (5011M) or Triton X-100 (0.1%, as total release of lactate dehydrogenase (LDH)) for 1 hr. The concentration of LDH in cell supernatant was analyzed using CytoTox 96 Non-Radioactive Cytotoxicity Assay. Data are expressed as mean±S.E.M. (n=6).

In this example, the cytotoxicity effect of the present compound was investigated by the measurement of LDH. Results are provided in FIG. 5.

As the data indicated, the present compound itself possessed no cytotoxicity toward the tested d-THP-1 cells.

Example 4 the Present Compound Inhibited Nigericin-Induced Pyroptotic Cell Death and Pyroptotic LDH Release in LPS-Primed d-THP-1 Cells Pyroptosis is a form of programmed cell death. In this process, immune cells recognize foreign danger signals within themselves, release pro-inflammatory cytokines, swell, burst, and die. In this example, the effects of the present compound on nigericin-induced pyroptotic cell death and LDH release were investigated, in which the pyroptosis phenomena was observed using Field Emission Scanning Electron Microscope, and LDH level was determined by enzymatic assay.

Figure 6:
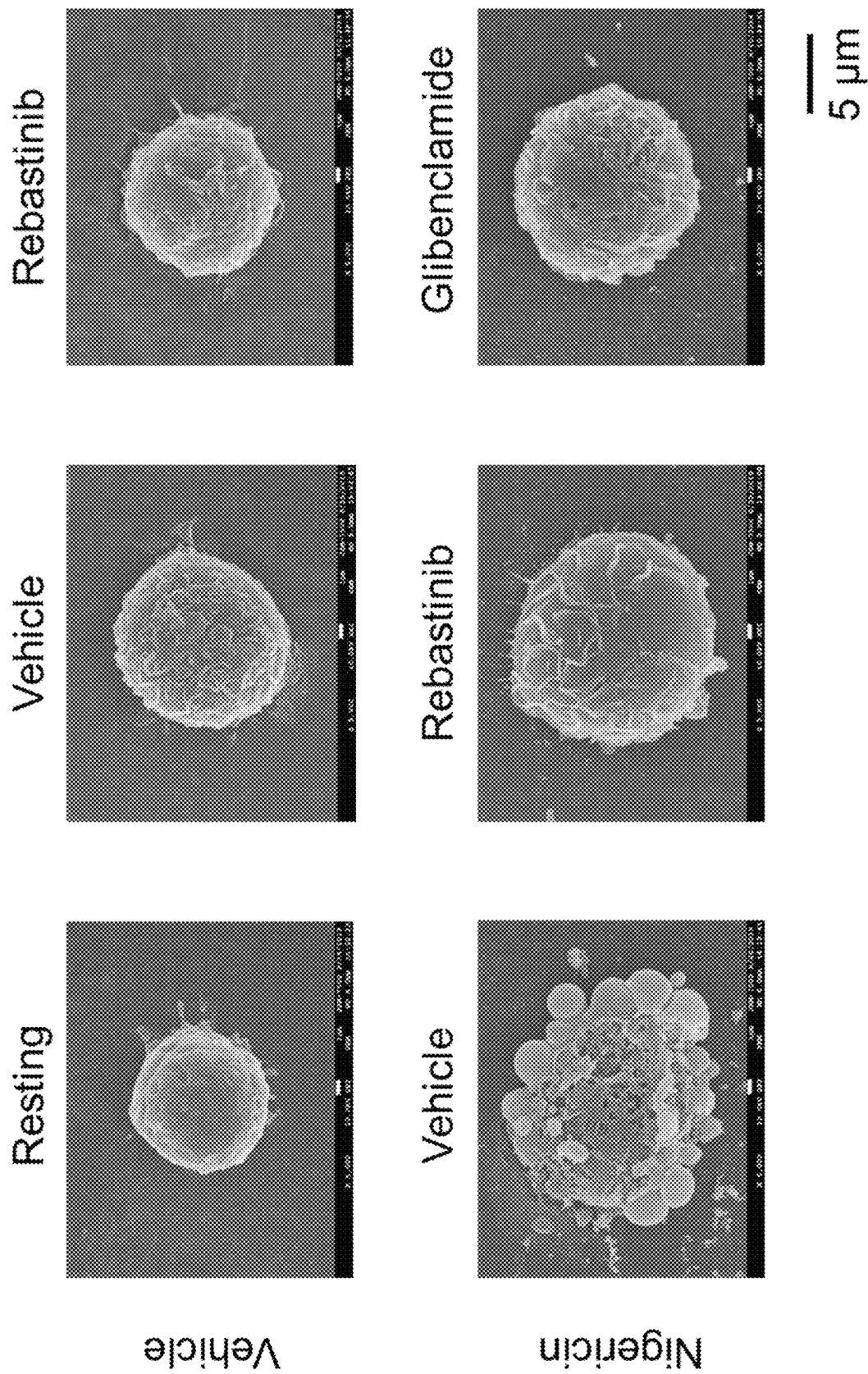
FIG. 6 Rebastinib inhibited nigericin-induced pyroptotic cell death in LPS-primed d-THP-1 cells. Pyroptotic cells were revealed by stimulating with nigericin (5 µM) for 30 min in LPS-primed d-THP-1 cells. LPS-primed d-THP-1 cells were incubated with DMSO (0.1%), rebastinib (1 µM) or glibenclamide (50 µM) for 30 min, and then stimulated with or without nigericin (511M) for 30 min. The represented images of pyroptotic cell death were shown by scanning electron microscopy (n=4).
Figure 7:
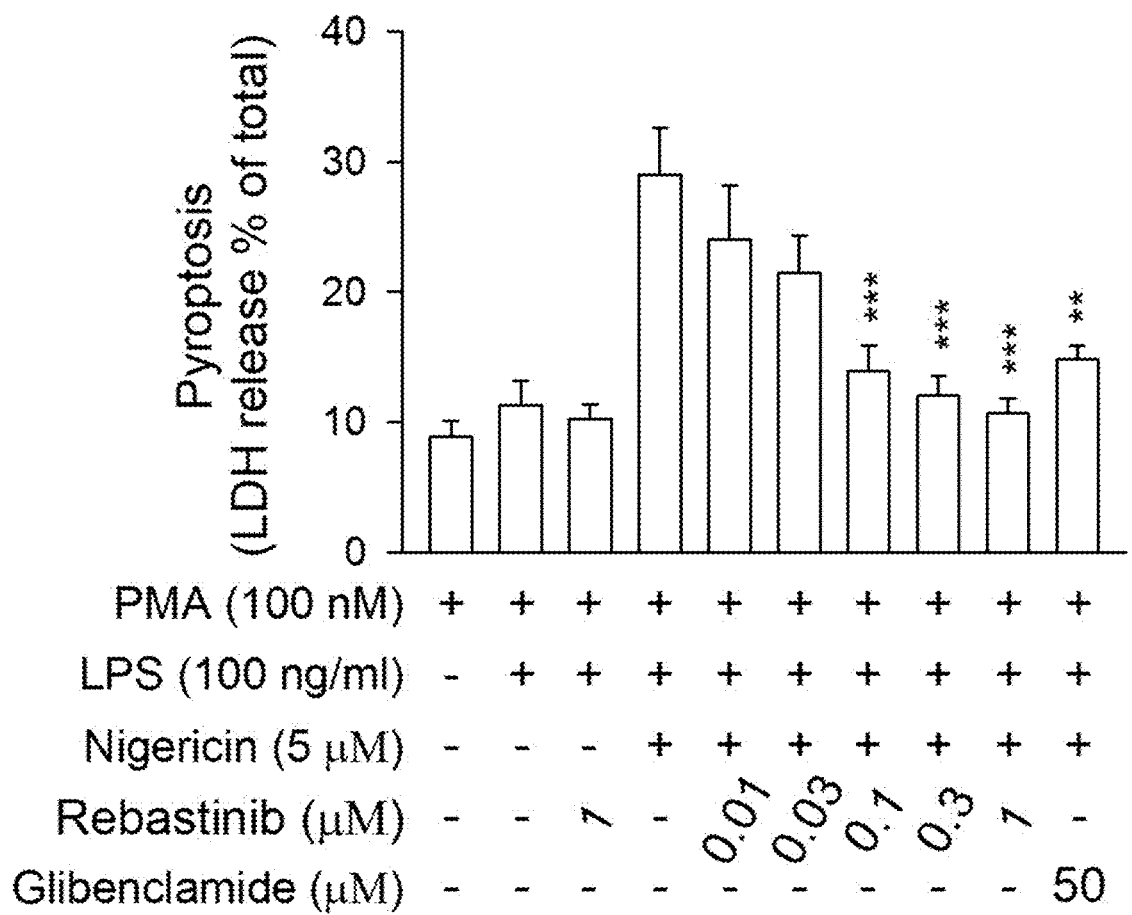
FIG. 7 Rebastinib inhibited nigericin-induced pyroptotic LDH release in LPS-primed d-THP-1 cells. LPS-primed d-THP-1 cells were incubated with DMSO (0.1%, as control), rebastinib (0.01-1 µM), glibenclamide (50 µM), or Triton X-100 (0.1%, as total LDH release) for 30 min, and then stimulated with or without nigericin (5 µM) for 30 min. The concentration of LDH in cell supernatant was analyzed using CytoTox 96 Non-Radioactive Cytotoxicity Assay. Data are expressed as mean±S.E.M. (n=6).  p<0.01; * p<0.001 compared with control.

Reference is made to FIG. 6, which are photographs of LPS-primed d-THP-1 cells stimulated with nigericin in the presence or absence of the present compound. As expected, nigericin induced swelling, bubbles, and lysis of LPS-primed d-THP-1 cells, while pre-treatment of the present compound, as well as glibenclamide (positive control), both significantly reduced the pyroptosis phenomena. Similar inhibitory effect of the present compound on the release of LDH was also observed (FIG. 7).

Example 5 the Present Compound Inhibited Nigericin-Induced Formation of ASC Speck in LPS-Primed d-THP-1 Cells A hallmark of inflammasome activation is the ASC speck, a micrometre-sized structure formed by the inflammasome adaptor protein ASC (apoptosis-associated speck-like protein containing a CARD), which consists of a pyrin domain (PYD) and a caspase recruitment domain (CARD). In this example, the effect of the present compound on nigericin-induced formation of ASC speck in LPS-primed d-THP-1 cells was observed using fluorescence microscope, and results are illustrated in FIG. 8.

Figure 8:
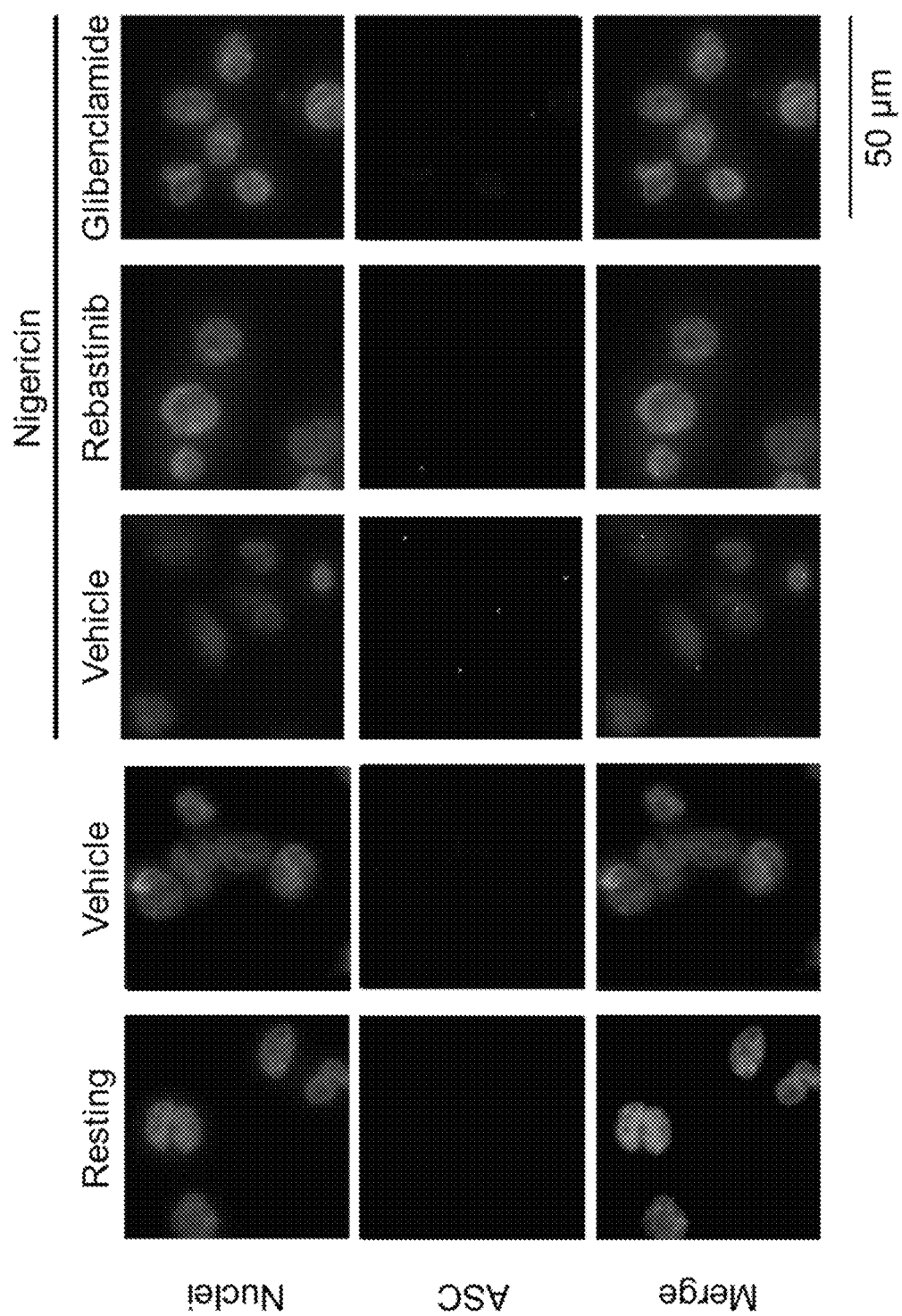
FIG. 8 Rebastinib inhibited nigericin-induced ASC speck formation in LPS-primed d-THP-1 cells. LPS-primed d-THP-1 cells were incubated with DMSO (0.1%, as control), rebastinib (1 µM) or glibenclamide (50 µM) for 30 min, and then stimulated with or without nigericin (5 µM) for 30 min. Cells were fixed by 4% paraformaldehyde and stained with anti-ASC and Hoechst 33342 (n=3). Images were visualized and captured by fluorescent microscopy (IX81, Olympus).

It is clear from the photographs provided in FIG. 8, formation of ASC speck was evident after nigericin treatment, however, if the cells were pre-treated with the present compound or glibenclamide (positive control), then the formation of ASC speck was greatly reduced. Data for this example clearly indicated that the present compound may suppress the activation of inflammasomes.

Example 6 the Present Compound Attenuated LPS/D-GalN-Induced Acute Liver Failure in Mice In this example, animal model of acute liver failure was used to investigate the effect of the present compound on acute liver failure. Briefly, animals were first subjected to LPS/D-GalN treatment (LPS: 40 μg/mL; D-GalN: 400 mg/mL) to create acute liver failure, then blood and tissue samples with or without treatment of the present compound were taken, which were then subjected to biochemistry and microscopy analysis. Results are provided in FIGS. 9 and 10.

Figure 9:
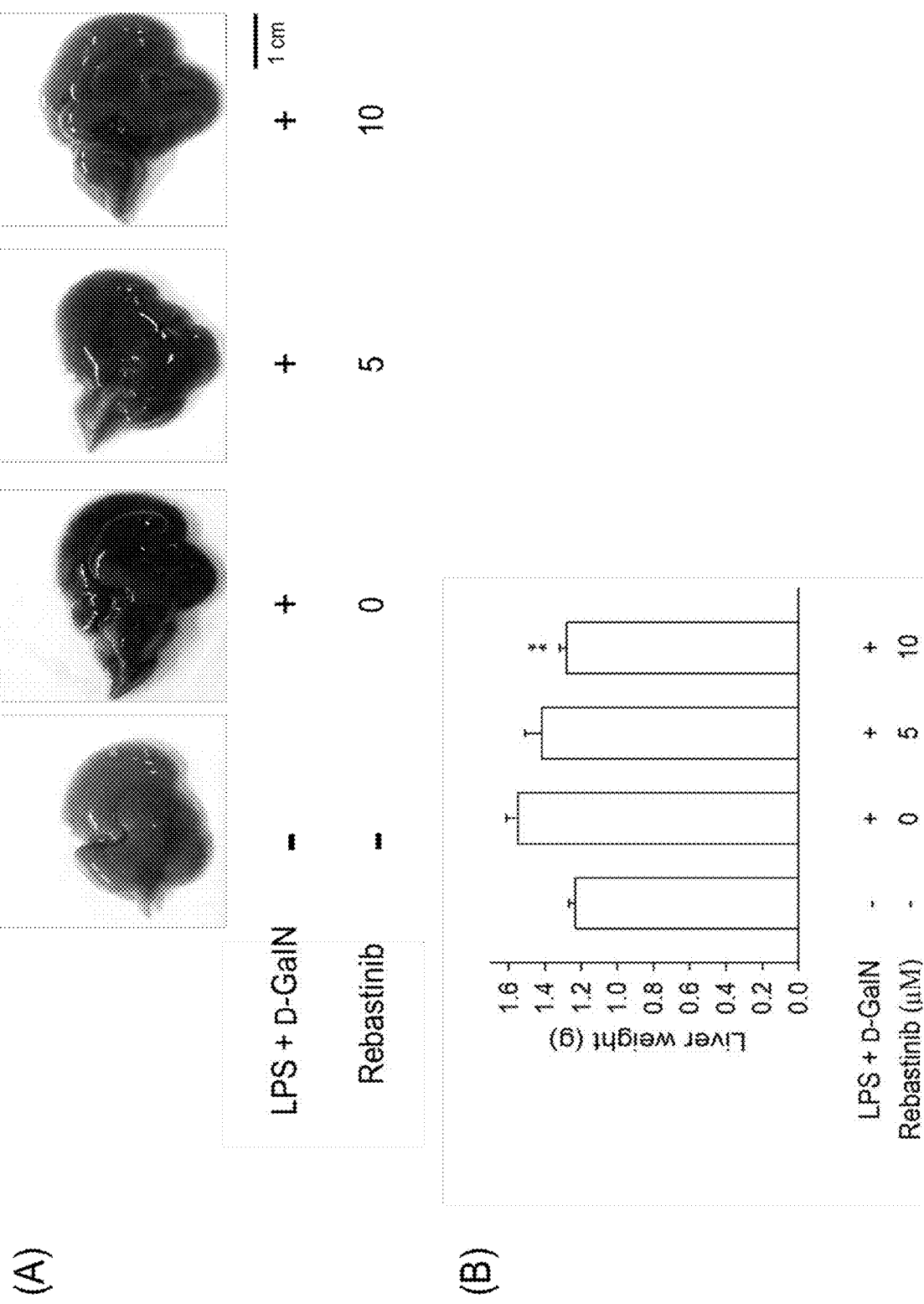
FIG. 9 Rebastinib attenuated lipopolysaccharide/D-galactosamine (LPS/D-GaIN)-induced acute liver failure in mice. 7-10 week-old mice (C57BL/6) were treated with vehicle control or rebastinib (5 or 10 mg/kg) by i.v. injection for 1 hr. The acute liver failure was induced by i.p. treatment of LPS (40 µg/kg)/D-GalN (400 mg/kg) for another 5 hr. (A) The representative gross images of liver morphology were taken by digital camera (scale bar: 1 cm). (B) The weights of whole livers are expressed as mean±S.E.M. (n=2-4). * p<0.05; compared with LPS/D-GalN treatment.
Figure 10:
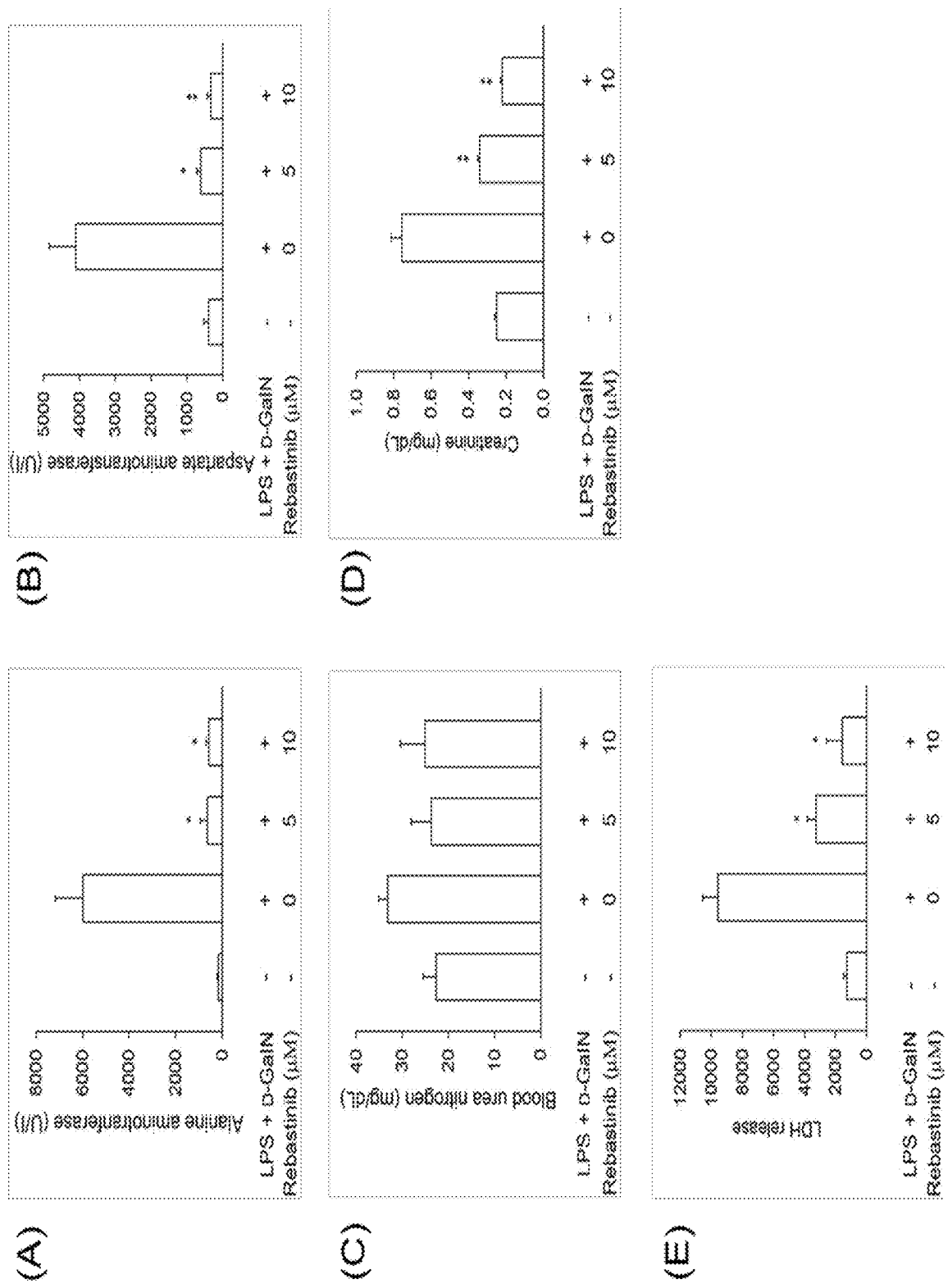
FIG. 10 Rebastinib attenuated the serum biochemical parameters in LPS/D-GalN-induced mice. 7-10 week-old mice (C57BL/6) were treated with vehicle or rebastinib (5 or 10 mg/kg) by i.v. injection and then treated with LPS (40 µg/kg)/D-GalN (400 mg/kg) by i.p. injection for another 5 hr, serum biochemistry parameters were assayed by automated clinical chemistry analyzer (Dri-Chem NX500i, Fujifilm). (A) aspartate transaminase (AST), (B) alanine transaminase (ALT), (C) blood urea nitrogen (BUN), (D) creatinine (CRE), and (E) LDH release were shown as mean±S.E.M. (n=2-4). * p<0.05; ** p<0.01 compared with LPS/D-GalN treatment alone.

As evident from FIG. 9, LPS/D-GalN treatment created liver injury, as the gross image of the injured liver tissue had a dark red color, which was a sign of tissue bleeding (FIG. 9, panel (A)). By contrast, the image taken from the liver sample of the animal treated with the present compound exhibited significant attenuation on the bleeding, as well as on the degree of inflammation, which was reflected on the decreases in the tissue weight (FIG. 9, panel (B)). Further, the respective levels of various indicators including ALT, AST, CRE and LDH for liver tissue failure decreased significantly after treatment of the present compound.

Example 7 the Present Compound Attenuated LPS-Induced ALI in Mice

In this example, animal model of ALI was used to investigate the effect of the present compound on ALI. Mice were intravenously injected with 50 ul of rebastinib (10 mg/kg) or an equal volume of solvent (vehicle). After 1 hr, mice were instilled with an intra-tracheal spray of 2 mg/kg LPS (dissolved in 40 μl 0.9% saline) or 0.9% saline under anesthesia. Five hrs later, mice were sacrificed and the lungs were collected. The lungs were fixed in 10% formalin for tissue section. The lung sections were stained with hematoxylin and eosin (H&E). Results are provided in FIG. 11.

Figure 11:
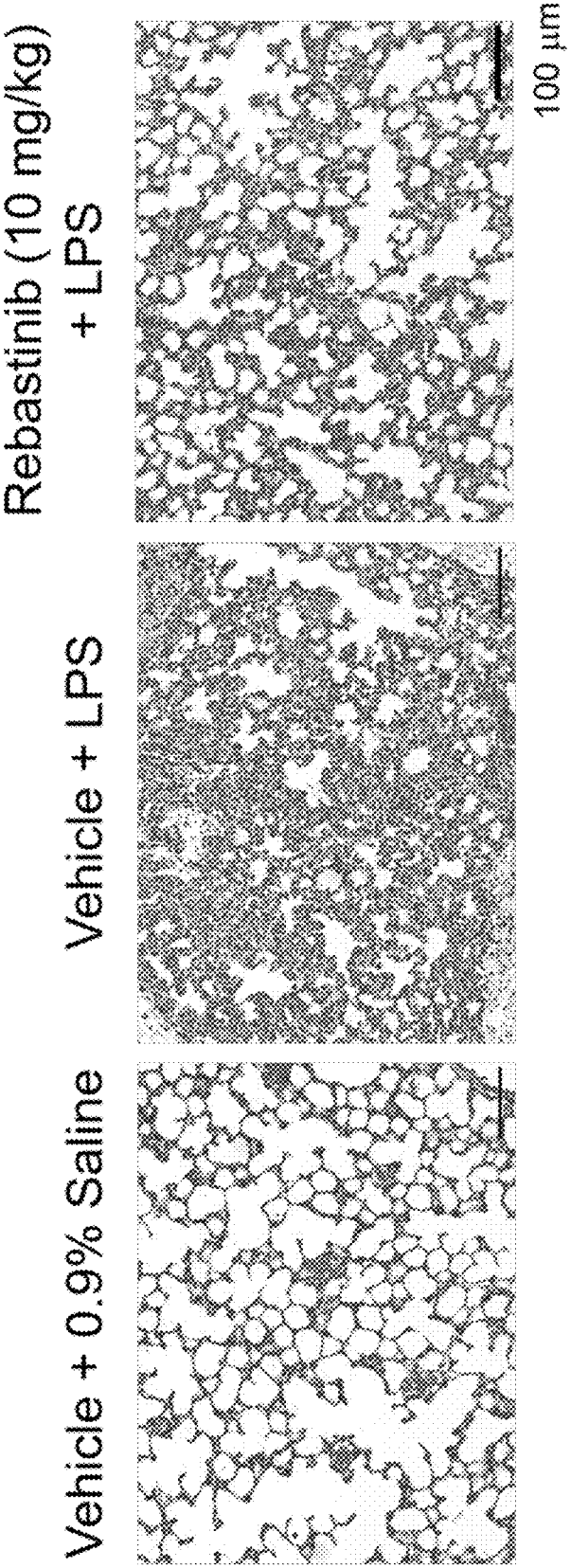
FIG. 11 Rebastinib attenuated LPS-induced acute lung injury (ALI). 7-8 week-old mice (C57BL/6) were treated with vehicle or rebastinib (10 mg/kg) by i.v. injection. After 1 hr, mice were instilled with an intra-tracheal spray of LPS (2 mg/kg, dissolved in 40 µL 0.9% saline) or 0.9% saline. 5 hr later, mice were sacrificed, and lung tissues were collected and stained with hematoxylin and eosin (H&E).

As shown in the photographs of FIG. 11, the lung tissue treated with solvent (i.e., vehicle) did not exhibit ALI. By contrast, morphology change and infiltration were observed in the lung tissue treated with LPS. As to the lung tissue pre-treated with rebastinib before being subjected to the spray of LPS, it was found that the LPS-induced morphology change and infiltration were significantly attenuated by the pre-treatment of rebastinib. This result indicates that rebastinib improves or cures ALI.

Taken together, the present compound may suppress activation of inflammasomes, thus, may serve as a candidate for the development of a medicament for treating diseases and/or conditions associated with activation of inflammasomes, including tissue injury such as acute liver failure and ALI.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the scope of the present disclosure.

What is claimed is:

1. A method of treating a subject having tissue injury comprising administering to the subject an effective amount of
4-[4-[(5-tert-butyl-2-quinolin-6-ylpyrazol-3-yl)-carbamoylamino]-3-fluorophenox y]-N-methylpyridine-2-carboxamide, a salt, a solvate or an ester thereof;
wherein the effective amount of
4-[4-[(5-tert-butyl-2-quinolin-6-ylpyrazol-3-yl)-carbamoylamino]-3-fluorophenox y]-N-methylpyridine-2-carboxamide is administered to the subject in the amount of 5-10 mg/Kg.

2. The method of claim 1, wherein the tissue injury is acute liver failure or ALI.

3. The method of claim 2, wherein the ALI is transfusion-related lung injury, ventilator-induced lung injury, bacteria-induced lung injury, or virus-induced lung injury.

4. The method of claim 1, wherein the subject is a mammal.

\* \* \* \* \*